United States Patent [19]

De Araujo et al.

[11] Patent Number: 5,215,917
[45] Date of Patent: Jun. 1, 1993

[54] **NUCLEOTIDE SEQUENCE ENCODING THE *TOXOPLASMA GONDII* P22 GENE**

[75] Inventors: Fausto G. De Araujo, Palo Alto; Jeffrey B. Prince, Mountain View; Jack S. Remington, Menlo Park, all of Calif.

[73] Assignee: Research Institute of Palo Alto Medical Foundation, Palo Alto, Calif.

[21] Appl. No.: 431,669

[22] Filed: Nov. 3, 1989

[51] Int. Cl.$^5$ .................... C12P 21/02; C12P 19/34; C12N 15/00; C12N 7/00; C12N 1/21; C12N 1/16; C12N 1/18; C07K 3/00; C07H 15/12

[52] U.S. Cl. .................... 435/252.33; 435/69.3; 435/91; 435/172.3; 435/235.1; 435/320.1; 435/252.3; 435/255; 435/256; 536/23.5; 536/23.7; 536/23.2; 536/23.4; 530/350

[58] Field of Search .............. 435/69.3, 91, 172.3, 435/255.1, 320.1, 252.3, 240.1, 255, 256, 252.33; 536/27; 530/350; 935/18, 31, 41, 58, 65, 73

[56] References Cited

U.S. PATENT DOCUMENTS 4,683,195  7/1987  Mullis et al. ................. 435/6

FOREIGN PATENT DOCUMENTS 0301961  1/1989  European Pat. Off.
PCT/US89/-
00884  9/1989  PCT Int'l Appl.

OTHER PUBLICATIONS

Woodward et al J. Immunological Methods vol. 78 pp. 143–153 (1985).
Young et al Proc. Natl Acad. Sci USA vol. 80 pp. 1194–1198 (1983).
Ellis et al. Nature vol. 302 pp. 536–538 (1983).
L. H. Kasper et al., in *The J. of Immul.*, 129(4):1294–1694 (1982).
L. H. Kasper et al., in *The J. of Immul.*, 132(1):443–449 (1984).
L. H. Kasper et al., in *The J. of Immul.*, 134(5):1694–1699 (1985).
E. Handman et al., in *The J. of Immul.*, 124(6):2578–2583 (1980).
G. Couvreur et al., in *Parasitology*, 97:1–10 (1988).
S. D. Sharma et al., in *The J. of Immunol.*, 133(6):2818–2820 (1984).
J. S. Remington et al., in *Inf. and Immun.*, 6(5):829–834 (1972).
L. D. Sibley et al., in *Infection and Immunity*, 55(9):2137–2141 (1987).
J. B. Prince et al., in *Mol. and Biochem. Parasit.*, 17:163–170 (1985).
J. F. Dubremetz et al. in *J. of Cell. Biochem.*, Supplement 13E, No. 0417, p. 102 (1989).
S. D. Sharma et al., in *The J. of Immul.*, 131(2):977–983 (1983).
A. M. Johnson et al., in *J. Protozol.*, 30(2):351–356 (1983).
S. D. Nagel and J. C. Boothroyd in *The J. of Biol. Chem.*, 264(10):5569–5574 (1989).

*Primary Examiner*—Joan Ellis
*Attorney, Agent, or Firm*—Cooley Godward Castro Huddleson & Tatum

[57] ABSTRACT

Genetic material encoding the P22 peptide of *Toxoplasma gondii* has been isolated and characterized. This genetic material allows the production of peptides for use in diagnosis or immunization or can itself be directly used in hybridization assays.

8 Claims, No Drawings

5,215,917

NUCLEOTIDE SEQUENCE ENCODING THE *TOXOPLASMA GONDII* P22 GENE

BACKGROUND OF THE INVENTION

1. Field of the Invention

This invention relates to the field of genetic engineering and more particularly to the identification and preparation of polynucleotide sequences and polypeptides useful for vaccine development and for detection of a toxoplasma infection by hybridization and immunological assays.

2. Description of the Background

Toxoplasmosis is caused by the protozoan parasite *Toxoplasma gondii*. The disease is traditionally associated with the developing fetus in whom it can cause severe neurological problems manifesting as hydrocephaly, mental retardation, or blindness. In healthy adults, the disease is typically mild, producing few if any symptoms.

Recently, the number of toxoplasmosis cases has dramatically increased as a result of an increase in persons who are in some way immunodeficient, such as resulting from post-transplantation therapy, neoplastic disease, or acquired immunodeficiency syndrome (AIDS). In such immunodeficient patients, the parasite can cause encephalitis, a potentially fatal form of the disease.

The current means of diagnosing toxoplasmosis are costly, time consuming, of limited sensitivity, and associated with substantial risks to the patient. Conventional procedures involving serologic techniques are very often not reliable because of severe immune dysfunction in AIDS patients and because of the recurrent nature of the disease. In pregnant women who are first tested for toxoplasmosis during pregnancy, it is critical to differentiate between current and past infection (currently done by comparing IgG and IgM titers over a period of time).

One problem that currently exists is obtaining sufficient quantities of suitable antigens both for the preparation of vaccines and for use as standards in immunological assays. Current techniques for providing antigen require the growth of protozoa in mice and the continual reinfection of new mice. Availability of a genetically engineered polypeptide antigen capable of being used either as a vaccine or an immunological standard would alleviate numerous problems with the current source of antigen.

Furthermore, the methods of treatment for prevention of toxoplasma infection are currently limited. There are no commercial vaccines available for the control of toxoplasmosis. Treatment of the disease is generally initiated and maintained with a drug regimen involving a combination of pyrimethamine and sulfadiazine. However, toxicity due to the drug treatment can be significant so that prophylactic drug therapy is not recommended except where cysts have actually been detected.

Accordingly, there remains a need for the development of diagnostic assays that reliably detect low levels of toxoplasma infection and of materials useful for the production of vaccines.

SUMMARY OF THE INVENTION

The present invention provides genetic material encoding a cell surface antigen of *T. gondii* known as P22. The genetic material can be used to produce polypeptides or proteins for use as vaccines or diagnostic reagents, or can be used as a source of probes that can be used in nucleic acid hybridization assays for the direct detection of toxoplasma infections. Specific genetic material and analytical techniques are disclosed in the following detailed description and the examples that follow.

DESCRIPTION OF SPECIFIC EMBODIMENTS

The present inventors have identified and obtained for the first time genetic material encoding the P22 antigen of the protozoan parasite *Toxoplasma gondii*. The P22 antigen, is a major surface antigen [See Kasper et al., *J. Imm.* (1983) 130: 2407–2412 ] and can be used for the production of vaccines or diagnostic standards (the latter for use, e.g., in immunoassays for detecting *T. gondii*). Accordingly, identification and isolation of this specified genetic material allows production of various biochemical components, such as antigens, diagnostic nucleic acid probes, and systems for producing the same, which find a variety of useful biological applications.

Since there is a known and definite correspondence between amino acids in a peptide and the DNA sequence that codes for the peptide, the nucleic acid sequence of a DNA or RNA molecule coding for a natural *T. gondii* protein (or any of the modified peptides later discussed) will readily be understood as indicating particular amino acid sequences, and such exemplary sequences of nucleotides and amino acids are shown in Table 1.

TABLE 1

Nucleotide sequence of one strand of DNA encoding *T. gondii* protein P22 and sequence of corresponding peptide. The DNA sequence is numbered beginning at the 5' terminus of a cloned sequence that contains the coding sequence. The reading frame begins with nucleotide 2. The peptide sequence of P22 is numbered with the first known amino acid encoded by the partial cDNA sequence as number 1.

P22 Sequence (Partial)

cDNA Sequence (coding sequence underlined)

| CTTGTTTGTT | GTGTTCAAGT | TCGCTCTTGC | GTCCACCACC | GAGACGCCAG | 50 |
| CGCCCATTGA | GTGCACTGCC | GGCGCAACGA | AGACTGTTGA | TGCACCCTCC | 100 |
| AGTGGTTCCG | TTGTCTTCCA | ATGTGGGGAT | AAACTAACCA | TCAGTCCCAG | 150 |
| TGGCGAAGGT | GATGTCTTTT | ATGGCAAGGA | ATGCACAGAC | TCGAGGAAGT | 200 |

TABLE 1-continued

| | | | | | |
|---|---|---|---|---|---|
| TGACGACTGT | CCTTCCAGGT | GCGGTCTTGA | CAGCTAAGGT | CCAGCAGCCC | 250 |
| GCGAAAGGTC | CTGCTACCTA | CACACTGTCT | TACGACGGTA | CTCCCGAGAA | 300 |
| ACCTCAGGTT | CTCTGTTACA | AGTGCGTTGC | CGAAGCAGGT | GCTCCCGCTG | 350 |
| GTCGAAATAA | TGATGGTTCT | AGCGCTCCGA | CGCCTAAAGA | CTGCAAACTC | 400 |
| ATTGTTCGCG | TTCCGGGTGC | CGATGGCCGT | GTCACATCTG | GGTTTGACCC | 450 |
| TGTGTCTCTC | ACGGGCAAGG | TTCTTGCTCC | CGGTCTCGCA | GGTTTGTTGA | 500 |
| TCACGTTTGT | GTAAAAGAAA | GGGCTGATGA | TTAAGTAGTC | AAAAGGTCAC | 550 |
| CGGAGAAGAG | TTGCGAAAGT | CGGTGAACGG | TGGTCGCCCT | CAGGGGTGCA | 650 |
| CTTTGTTGTT | TTGCTTGAAG | ATGCTCTTCC | TATAAATCTT | CCGAAAATGT | 700 |
| TTCTCCGCAT | GACGGGGGTT | GAGCGAAGTT | GGTGGTAACG | GGAATAATTA | 750 |
| AACGGGGATA | TCATTCCCCG | TAGCGGGGTG | GATGGGTGCC | TCCGGGGCTG | 800 |
| CCGCAGTTCT | GTTCTCCGAA | GTGACTCCAG | GTGGGCCGTG | CGGCTTTTGT | 900 |
| CTTTTTCGTG | AGAGCGGTCC | GACCCTGCAA | TTCTCATGCC | TCCGCTTCGA | 950 |
| AATTGTCGTG | CAAAGAAAAC | GTTGTTGAGG | GGTGGGATTG | CGATTGTTCT | 1000 |
| TGGCGTAGAT | CCTGGGAGGA | ACGCGAGAAA | ATGTATTTCC | GGATCTGCGA | 1050 |
| TTATGTGACA | GAGGAACTTG | TTTGCCCACA | CACTGCTGCA | GTAAAAAAAA | 1100 |
| AAAAAA | | | | | |

Amino Acid Sequence

| | | | | |
|---|---|---|---|---|
| LFVVFKFALA | STTETPAPIE | CTAGATKTVD | APSSGSVVFQ | 40 |
| CGDKLTISPS | GEGDVFYGKE | CTDSRKLTTV | LPGAVLTAKV | 80 |
| QQPAKGPATY | TLSYDGTPEK | PQVLCYKCVA | EAGAPAGRNN | 120 |
| DGSSAPTPKD | CKLIVRVPGA | DGRVTSGFDP | VSLTGKVLAP | 160 |
| GLAGLLITFV | | | | |

The invention has specifically contemplated each and every possible variation of polynucleotide that could be made by selecting combinations based on the possible codon choices listed in Table 1 and Table 2 (below), and all such variations are to be considered as being specifically disclosed.

Since the DNA sequence of the P22 gene has been identified, it is possible to produce a DNA gene entirely by synthetic chemistry, after which the gene can be inserted into any of the many available DNA technology. Thus the present invention can be carried out using reagents, plasmids, and microorganisms which are freely available and in the public domain at the time of filing of this patent application.

For example, nucleotide sequences greater than 100 bases long can be readily synthesized on an Applied Biosystems Model 380A DNA Synthesizer as evidenced by commercial advertising of the same (e.g., Genetic Engineering News, November/December 1984, p. 3). Such oligonucleotides can readily be spliced using, among others, the technique of preparing overlapping complementary sequences (e.g., 1-100 of coding strand, 0-50 and 51-150 of complementary strand, 101-200 of coding strand, etc.), followed by hybridizing and ligating the strands. Such techniques are well known and are described in detail in, for example, Davis et al., Basic Methods in Molecular Biology, Elsevier Science Publ. Co., Inc., New York (1986).

Furthermore, automated equipment is also available that makes direct synthesis of any of the peptides disclosed herein readily available. In the same issue of Genetic Engineering News mentioned above, a commercially available automated peptide synthesizer having a coupling efficiency exceeding 99% is advertised (page 34). Such equipment provides ready access to the peptides of the invention, either by direct synthesis or by synthesis of a series of fragments that can be coupled using other known techniques.

In addition to the specific polypeptide sequences shown in Table 1, peptide fragments based on these sequences and fragments representing minor variations thereof will have the biological activity of the various peptides. For example, fragments of the P22 peptide sequence can readily be prepared and screened for recognition by immunoglobulins specific for the P22 antigen itself. Peptide synthesizers can be used to prepare small polypeptide fragments (e.g., less than 100 amino acids) or techniques of genetic engineering can be used to prepare larger fragments. A simple screening procedure that will identify suitable polypeptide fragments consists of preparing monoclonal antibodies to the P22 antigen, attaching the antibodies to an affinity column, and capturing peptide fragments that are retained by the bound antibody. Polyclonal antisera can be used instead of monoclonal antibodies if desired. This technique has been demonstrated by the ability of antibodies to identify clones containing segments of the P22 gene, as described in detail in the examples that follow.

The ability to prepare and select appropriate immunologically active fragments from a larger protein is well known in the art and is described in a number of publications, including patents. See, for example, U.S. Pat. No. 4,629,783, which described the preparation of immunologically active fragments of viral proteins.

One common variation is the preparation of a polypeptide of the invention in the form of a fused polypeptide. Such peptides are typically prepared by using the promoter region of a gene known to be expressed in a host and inserting nucleotides that encode all or a major portion of the amino acid sequence of the invention into the genetic sequence for the host protein. Examples of such fused proteins include β-galactosidase fused proteins.

Another technique for preparing immunologically active peptide fragments is to synthesize a series of amino acids of from 5-100 amino acids in length (or any intervening length, such as 10, 15, or any other multiple of 2, 3, or 5 in this range) and screen for immunological activity using an antiserum (or monoclonal antibody). The fragments would be selected along the entire length of the peptide to optimize cross-reactivity (e.g., a series of peptides 20 amino acids in length and comprising $AA_1$-$AA_{20}$, $AA_5$-$AA_{25}$, $AA_{10}$-$AA_{30}$, etc.). The selected fragment would then correspond to particularly useful corresponding nucleotide sequences that could be used to produce large amounts of the peptide for use as described herein.

In addition, minor variations of the previously mentioned peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid (i.e., a conservative replacement) will not have a major effect on the biological activity of the resulting molecule, especially if the replacement does not involve an amino acid at a binding site or other site of biologic activity. Whether a change results in a functioning peptide can readily be determined by direct analysis for function in an immunization or in a diagnostic test that relies on immunogenic specificity. Examples of this process are described later in detail. Peptides in which more than one replacement has taken place can readily be tested in the same manner. Preferred peptides differ at no more than 12, more preferably no more than 5, amino acids in any contiguous group of 20 amino acids. Standard conservative groups of amino acids are shown in parenthesis using the one-letter amino acid code: nonpolar (A,V,L,I,P,M); aromatic (F,T,W); uncharged polar (G,S,Y,C,N,Q); acidic (D,E); basic (K,R,H). The aromatic amino acids are sometimes considered to belong to the broader-defined nonpolar (F,W) or uncharged polar (T) groups.

Other DNA molecules that code for such peptides can readily be determined from the list of codons in Table 2 and are likewise contemplated as being equivalent to the DNA sequence of Table 1. In fact, since there is a fixed relationship between DNA codons and amino acids in a peptide, any discussion in this application of a replacement or other change in a peptide is equally applicable to the corresponding DNA sequence or to the DNA molecule, recombinant vector, or transformed microorganism in which the sequence is located (and vice versa).

TABLE 2

| GENETIC CODE | |
|---|---|
| Alanine(Ala, A) | GCA, GCC, GCG, GCT |
| Arginine(Arg, R) | AGA, AGG, CGA, CGC, CGG, CGT |
| Asparagine(Asn, N) | AAC, AAT |
| Aspartic acid(Asp, D) | GAC, GAT |
| Cysteine(Cys, C) | TGC, TGT |
| Glutamine(Gln, Q) | CAA, CAG |
| Glutamic acid(Glu, E) | GAA, GAG |
| Glycine(Gly, G) | GGA, GGC, GGG, GGT |
| Histidine(His, H) | CAC, CAT |
| Isoleucine(Ile, I) | ATA, ATC, ATT |
| Leucine(Leu, L) | CTA, CTC, CTG, CTT, TTA, TTG |
| Lysine(Lys, K) | AAA, AAG |
| Methionine(Met, M) | ATG |
| Phenylalanine(Phe, F) | TTC, TTT |
| Proline(Pro, P) | CCA, CCC, CCG, CCT |
| Serine(Ser, S) | AGC, AGT, TCA, TCC, TCG, TCT |
| Threonine(Thr, T) | ACA, ACC, ACG, ACT |
| Tryptophan(Trp, W) | TGG |
| Tyrosine(Tyr, Y) | TAC, TAT |
| Valine(Val, V) | GTA, GTC, GTG, GTT |
| Termination signal | TAA, TAG, TGA |

Key: Each 3-letter triplet represents a trinucleotide of DNA having a 5'end on the left and a 3'end on the right. The letters stand for the purine or pyrimidine bases forming the nucleotide sequence: A = adenine, G = guanine, C = cytosine, and T = thymine. The RNA code is the same except that U (uracil) replaces T.

In addition to the specific nucleotides listed in Table 1, DNA (or corresponding RNA) molecules of the invention can have additional nucleotides preceeding or following those that are specifically listed. For example, poly A can be added to the 3'-terminal; a short (e.g., fewer than 20 nucleotides) sequence can be added to either terminal to provide a terminal sequence corresponding to a restriction endonuclease site, stop codons can follow the peptide sequence to terminate translation, and the like. Additionally, DNA molecules containing a promoter region or other control region upstream from the gene can be produced. All DNA molecules containing the sequences of the invention will be useful for at least one purpose since all can minimally be fragmented to produce oligonucleotide probes and be used in the isolation or detection of DNA from biological sources.

By "equivalent" is meant, when referring to two nucleotide sequences, that the two nucleotide sequences in question encode the same sequence of amino acids. "Complementary," when referring to two nucleotide sequences, means that the two sequences are capable of hybridizing, preferably with less than 5%, more preferably with no mismatches between opposed nucleotides. The term "substantially" preferably means at least 95% by weight, more preferably at least 99% by weight, and most preferably at least 99.8% by weight. The term "isolated" as used herein refers to peptide, DNA, or RNA separated from other peptides, DNAs, or RNAs, respectively, and being found in the presence of (if anything) only a solvent, buffer, ion or other component normally present in a biochemical solution of the same. "Isolated" does not encompass either natural materials in their native state or natural materials that have been separated into components (e.g., in an acrylamide gel) but not obtained either as pure substances or as solutions. The phrase "replaced by" or "replacement" as used herein does not necessarily refer to any action that must take place but to the peptide that exists when an indicated "replacement" amino acid is present in the same position as the amino acid indicated to be present in a different formula (e.g., when leucine instead of valine is present at amino acide 48 of P22.

Salts of any of the peptides described herein will naturally occur when such peptides are present in (or isolated from) aqueous solutions of various pHs. All salts of peptides having the indicated biological activity are considered to be within the scope of the present invention. Examples include alkali, alkaline earth, and other metal salts of carboxylic acid residues, acid addition salts (e.g., HCl) of amino residues, and zwitter ions formed by reactions between carboxylic acid and amino residues within the same molecule.

Peptides of the invention can be prepared for the first time as homogeneous preparations, either by direct synthesis or by using a cloned gene or a fragment thereof as described herein. The P22 peptides were previously enriched by affinity chromatography and/or gel electrophoresis, but the resulting material was not free of all other toxoplasma materials.

Although genes and corresponding proteins can be prepared by the totally synthetic techniques discussed above, in preferred embodiments of the invention genetic information is obtained from natural sources and identified as described herein. The genetic material is first obtained in the form of a gene library, using any of numerous existing techniques. The first of these is to randomly shear genomic DNA and insert this sheared material into expression vectors. If enough recombinants are generated, there is a good probability of having at least one recombinant in the population which is expressing a fusion protein corresponding to the antigen of interest. In practice, for a genome the size of *T. gondii* (about $7 \times 10^7$ bp), at least $5 \times 10^6$ independent recombinants are needed. This allows for the entire genome to be represented by recombinants where at least one insert will exist with one of its ends falling within any 10-base-pair region. Allowing for only 1 in 6 such insertions being in the correct orientation and reading frame, functional recombinants should exist in such a library with fusions corresponding to every 60 base pairs.

Another strategy for preparing gene libraries is to make complementary DNA (cDNA) copies of the total mRNA population of the parasite and to clone these as recombinant molecules in expression vectors. Other investigations indicated that introns were present within the coding regions of other *T. gondii* genes. Although introns do not preclude use of sheared genomic DNA, they increase the number of recombinants which must be screened and make further analyses substantially more complicated. Based on this result, use of a cDNA library to obtain *T. gondii* genes is preferred.

As described in detail in the examples that follow, the sequence of the gene encoding the P22 peptide was obtained from the sequences of the clones obtained in this fashion.

Polyclonal antisera to P22 can also be used to screen a cDNA library in order to locate the P22 gene. Recombinants initially identified in this manner have been found to contain different genes, implying that at least some fortuitous cross-reaction with anti-P22 sera occurs. The true P22 gene can be obtained by screening with monoclonal antibody against P22, and its identity verified by preparing antisera against each of the fusion proteins obtained in the initial screening. These sera are then used in Western blot analyses against a lysate of *T. gondii*. Only antisera from the fusion product of the P22 gene will show reactivity predominantly or exclusively to P22.

A clone obtained in the manner described above has been fully sequenced. This sequence contains the partial protein-coding sequence of the P22 gene as shown in Table 1. The primary translation product has a hydrophobic C-terminus which is not followed by any charged residues. This is apparently diagnostic of a process originally reported in trypanosomes whereby the hydrophobic polypeptide segment is replaced by a glycolipid anchor. The presence of such a glycolipid anchor in the major surface antigens of *T. gondii*, including P22, has been reported.

Now that this sequence has been determined, it is no longer necessary to go through these steps to obtain the genetic material of the present invention. The polymerase chain reaction (PCR) technique can now be used to isolate genes from natural sources in a simpler and more direct manner. Since *T. gondii* specimens are readily available from sources such as the American Type Culture Collection of Rockville, Md., and since PCR probes can be prepared using the sequences set forth in this specification, it is possible to obtain any desired segment of the sequences set forth herein using the PCR technique and commercially available sources of the *T. gondii* genomic material.

Although only a partial cDNA coding sequence is being disclosed for the P22 gene, this sequence can be used by those skilled in the art to isolate and determine the remaining coding sequence. Moreover, the DNA sequence disclosed represents about 75% of the expected coding sequence and therefore is likely to contain the predominant functional region of the molecule. This has already been demonstrated by the ability of fusion polypeptides corresponding to portions of this region to react with antibodies in human sera, as described in the examples below.

The gene encoding the P22 antigen can be used for the production of full or modified peptides using standard techniques of manipulating and growing unicellular microorganisms. Antigens which are candidates for vaccine development and/or diagnostic reagents will include those recognized by serum from infected patients. Additionally, any of the genetic sequences can be used as probes in hybridization assays.

Although the techniques set forth above, when used in combination with the knowledge of those skilled in the art of genetic engineering and the previously stated guidelines, will readily enable isolation of the desired gene and its use in recombinant DNA vectors now that sufficient information is provided to locate the gene, other methods which lead to the same result are also known and may be used in the preparation of recombinant DNA vectors of this invention.

Expression of *T. gondii* proteins can be enhanced by including multiple copies of the gene in a transformed host; by selecting a vector known to reproduce in the host, thereby producing large quantities of protein from exogenous inserted DNA (such as pUC8; ptac12; pIN-III-ompA1, 2, or 3; pOTS; pAS1; or pKK223-3); or by other known means of enhancing peptide expression.

In all cases, a *T. gondii* protein will be expressed when the DNA sequence is functionally inserted into the vector. By "functionally inserted" is meant in proper reading frame and orientation, as is well understood by those skilled in the art. Typically, a gene will be inserted downstream from a promoter and will be followed by a stop codon, although production as a hybrid protein (possibly followed by cleavage) may be used, if desired.

In addition to the above general procedures which can be used for preparing recombinant DNA molecules and transformed unicellular organisms in accordance with the practices of this invention, other known techniques and modifications thereof can be used in carrying out the practice of the invention. In particular, techniques relating to genetic engineering have recently undergone explosive growth and development. Many recent U.S. patents disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering.

The implications of the present invention are significant in that useful amounts of *T. gondii* proteins and genetic material of the invention will become available for use in the development of hybridization assays or in any other type of assay utilizing these materials as a reagent for use in diagnosis, immunization, therapeutics, and research. Methods of using genetic material in a hybridization assay are disclosed in U.S. Pat No. 4,683,202, which is herein incorporated by reference. Transferring the *T. gondii* cDNA which has been isolated to other expression vectors will produce constructs which improve the expression of a *T. gondii* polypeptide in *E. coli* or express the polypeptide in other hosts.

Particularly contemplated is the isolation of genes from these and related organisms that express *T. gondii* protein using oligonucleotide probes based on the principal and variant nucleotide sequences disclosed herein. Such probes can be considerably shorter than the entire sequence but should be at least 10, preferably at least 14, nucleotides in length. Intermediate oligonucleotides from 20 to 500, especially 30 to 200, nucleotides in length provide particularly specific and rapid-acting probes. Longer oligonucleotides are also useful, up to the full length of the gene. Both RNA and DNA probes can be used.

In use, the probes are typically labelled in a detectable manner (e.g., with $^{32}P$, $^{3}H$, biotin, or avidin) and are incubated with single-stranded DNA or RNA from the organism in which a gene is being sought. Hybridization is detected by means of the label after single-stranded and double-stranded (hybridized) DNA (or DNA/RNA) have been separated (typically using nitrocellulose paper). Hybridization techniques suitable for use with oligonucleotides are well known.

Although probes are normally used with a detectable label that allows easy identification, unlabelled oligonucleotides are also useful, both as precursors of labeled probes and for use in methods that provide for direct detection of double-stranded DNA (or DNA/RNA). Accordingly, the term "oligonucleotide probe" refers to both labeled and unlabeled forms.

In addition to those uses previously enumerated, proteins produced using the genetic information set forth above have numerous uses in diagnosis and prophylaxis. For example, peptides and peptide fragments can be used in enzyme-linked immunosorbent assays (ELISA) for detection of IgG, IgM, IgA, and IgE antibodies to *T. gondii* in human sera. Antigens of the invention can also be used in the HS/AC agglutination assay described in Thulliez et al., *Path. Biol.,* 34: 173–177 (1986) for the detection of agglutinating antibodies in human sera. Additionally, competitive antibody enzyme immunoassays (CEIA) can be used to detect antibodies in human sera that compete with monoclonal antibodies directed against the P22 antigen. Peptides and peptide fragments of the invention can also be used for the production of monospecfic polyclonal antibodies for use in an antigenemia test to detect circulating antigen in patient samples, as described in Araujo et al., *J. Infect. Dis.,* 141: 144–150 (1980).

Additonally, it is possible to determine efficacy of any antigenic peptides or peptide fragments of the present invention for use as a vaccine. The peptide is used to immunize mice either alone, conjugated with purified protein derivative (PPD), incorporated into liposomes or incorporated with Quil A into an immunostimulating complex (ISCOM), or combined with an adjuvant (Freund's complete adjuvant, Freund's incomplete adjuvant, saponin, muramyl dipeptide, interferon-λ, or other adjuvants that might be developed). Immunization will be by the oral route or by multiple injections intraperitoneally or subcutaneously, following which the serological response, delayed-type hypersensitivity (DTH), and cell-mediated immune response will be measured using standard techniques. The immunized mice will be challenged with tachyzoites or cysts of virulent and avirulent strains of *T. gondii*, and the animals will be examined at various times until death for the development of *T. gondii* cysts in the brain and in the skeletal and heart muscle.

The invention now being generally described, the same will be better understood by reference to the following examples which are provided for purposes of illustration only and are not to be considered limiting of the invention unless so specified.

EXAMPLES

Example 1: Identification of P22 Genetic Material

An expression library was constructed in the vector λgt11 with cDNA made from poly(A)[30] RNA of the RH strain of *T. gondii*. This vector provides for expression of the inserted cDNAs as polypetides fused to β-galactosidase. The technique used was essentially that of Huynh et al., "Construction and screening cDNA libraries in λgt10 and λgt11" in *DNA Cloning*, Glover, D. M., ed., vol. I, pp. 49-78, IRL Press, Oxford.

Briefly, cDNA was synthesized from 2.2 μg of tachyzoite poly(A)[30] RNA template using AMV reverse transcriptase, and the second strand was synthesized with DNA polymerase I Klenow fragment followed by S1 nuclease treatment. The double-stranded cDNA was fractionated by chromatography on Sepharase CL-4B, blunt-ended with DNA polymerase I, methylated with EcoRI methylase, and EcoRI linkers added. Following removal of excess linkers by digestion with EcoRI and chromatography on Sephadex G-150, the cDNA was ligated into the EcoRI site in the lacZ gene of λgt11 and packaged in vitro. The library consisted of $0.6 \times 10^5$ recombinant phage (colorless-pfu) prior to amplification; the names of clones isolated from this library are prefixed with a "c".

Monoclonal antibodies (MAbs) 87-21-5A6 and 87-21-6D-10, which were raised against a membrane-enriched fraction of *T. gondii* RH strain tachyzoites and which recognize a single major antigen with an apparent size of 22kDA in Western blots of reduced or unreduced *T. gondii* tachyzoites, are both positive in the Sabin-Feldman dye test (for complement-fixing antibodies) and the immunofluorescent antibody test using live *T. gondii* tachyzoites. These data suggest that both MAbs recognize P22 on the parasite surface. When these MAbs were used to screen the cDNA expression library in λgt11, two clones were obtained, designated c86 and c88.

TABLE 3

| λgt11 Clone | Isolation Method | cDNA Insert Sequence[a] | Expressed Polypeptide[b] |
|---|---|---|---|
| c88 | 5A6[c] | 1-909 | 1-170 |
| c86 | 6D10[d] | 253-1055 | 85-170 |

[a]Numbers correspond to nucleotide positions of the composite partial P22 cDNA sequence shown in TABLE 1.
[b]Numbers correspond to amino acid residues of the deduced partial P22 protein sequence shown in TABLE 1.
[c]MAb 87-21-5A6 used as an antibody probe.
[d]MAb 87-21-6D10 used as an antibody probe.

Example 2: Composite cDNA and Deduced Amino Acid Sequence of P22

Sequencing in M13 and mp18 or mp19 was performed by the dideoxy chain terminator method using [35S]dATP and DNA polymerase, or Sequenase™ DNA polymerase. For sequencing in λgt11, template/primer hybrids were prepared by the method of Chen and Seeburg, *DNA*, 4: 165-170 (1985).

Sequence analysis revealed that clones c88 and c86 contain overlapping DNA segments that together encompass 1056 bp of cDNA sequence. As shown in Table 1, the composite cDNA sequence contains a 5' open reading frame of 510 bp (encoding a polypeptide with MW of 17,364) and a 14-bp poly(A) tail at the 3'end. These two clones thus comprise about 75% of the expected coding sequence. The portions of the composite sequence present in each clone are indicated in Table 3. The putative polypeptide encoded by the composite cDNA contains no N-linked glycosylation sites but has a hydrophobic C-terminus characteristic of surface proteins that possess a glycolipid anchor.

Example 3: Hybridization of *T. gondii* Nucelic Acids with P22 cDNA Probes

For isolation of DNA or total RNA for blot analyses, tachyzoites of the RH strain were grown in and harvested from the peritoneal cavities of mice as previously described in Prince et al., *Mol. Biochem. Parasitol.* (1985) 17: 163-170.

Total RNA was isolated from *T. gondii* tachyzoites by the guanidinium thiocyanate extraction method, and poly(A)+RNA was selected by passage over oligo(dT)-cellulose. Tachyzoite DNA was isolated by lysis with sodium dodecyl sulfate (SDS) and proteinase K, as described by Davis et al., *Basic Methods in Molecular Biology*, Elsevier Science Publ. Co., Inc., New York (1986).

When genomic DNA of the RH strain of *T. gondii* was digested with restriction enzymes that do not cut within the c88 insert and was then probed with radiolabeled c88 insert, the probe hybridized with single bands for all enzymes tested. These data suggest that the P22 gene exists as a single copy in the tachyzoite haploid genome. Consistent with the latter result, the cloned cDNAs hybridize in Northern blots to a single RNA band about 1.5 kb in size.

Example 4: Antigenicity of Recombinant P22 Fusion Proteins and Confirmation of Gene Identity To examine the recombinant β-galactosidase fusion proteins synthesized by clones c88 and c86, lysogens were prepared in *E. coli* Y1089 and the cell lysates (prepared according to Huynh et al., op. cit.) analyzed by SDS-PAGE.

SDS-PAGE was performed according to the method of Laemmli, *Nature*, 227: 680-685 (1970). Molecular weight markers were Diversified Biotech mid range-prestained: phosphorylase b (94400), glutamate dehydrogenase (55000), ovalbumin (43000), lactate dehydrogenase (36000), carbonic anhydrase (29000), lactoglobulin (18400), cytochrome c (12400); BioRad high molecular weight; myosin (200000), β-galactosidase (116250), phosphorylase b (97400), bovine serum albumin (66200), ovalbumin (42699), carbonic anhydrase (31000), soybean trypsin inhibitor (21500), lysozyme (14400). After separation by SDS-PAGE, proteins were electrophoretically transferred to nitrocellulose paper and reacted with antibody according to the immunoblotting technique of Towbin et al., *Proc. Natl. Acad. Sci. USA*, 76: 4350-4354 (1979). Prior to use in immunoblots of lysogen lysates, all sera were preincubated with a wild-type λgt11 lysogen lysate to remove most anti-*E. coli*/λgt11 antibodies.

Both the c86 and c88 lysogens produced quantities of fusion protein sufficient to be readily visualized by staining the gels with Coomassie blue. In addition, when the lysogen lysates were blotted onto nitrocellulose and probed with the two anti-P22 MAbs, both fusion proteins reacted specifically with both 87-21-5A6 and 87-21-6D10 MAbs.

Further immunoblot analysis revealed that the c86 and c88 fusion proteins also reacted specifically with IgG antibodies in the sera of humans infected with *T. gondii*. Each of the serum samples from two patients with acute *T. gondii* infection (dye test=8000 for both; double-sandwich IgM ELISA=11.4 and 13.4) reacted specifically with the fusion proteins. Under the test conditions, these sera did not react with β-galactosidase in the lysate prepared from a wild-type λgt11 lysogen.

In addition, no reaction was observed between the fusion proteins and antibodies in the sera of humans not infected with *T. gondii*. Since the c86 fusion protein contains only the terminal 86 amino acids of the primary translation product, the reactive epitopes for both the MAbs and the antibodies in the human sera must reside within that region.

To determine the size of the mature parasite antigen encoded by the recombinant clones, c88 fusion protein was employed to affinity purify IgG antibodies for use in an immunoblot of *T. gondii* lysate.

Briefly, crude lysate of the recombinant lysogen was subjected to SDS-PAGE on a 7% acrylamide gel, electrophoretically transferred to nitrocellulose, and a thin, horizontal strip containing the recombinant fusion protein excised and incubated with immune human serum, diluted 1:50 in TBS, 5% nonfat dry milk, 0.05% Tween-20. After washing the strip to remove unbound antibodies, bound antibody was eluted by incubation in 0.2 M glycine-HCl, pH 2.5, 0.15 M NaCl, 0.05% Tween-20 for 15 minutes at 20° C. The eluate was immediately neutralized to pH 7.4 by addition of Tris base and adjusted to 5% nonfat dry milk, 0.1% $NaN_3$. Additional details on this technique can be found in Hall et al., *Nature,* 311: 379-382 (1984).

Human IgG antibodies specifically bound to and then eluted from c88 fusion protein on nitrocellulose paper were used to probe a blot of whole lysate of the RH strain of *T. gondii*. The eluted antibodies reacted with a single band with an apparent molecular mass of 22 kDa. These data serve to verify that the cloned cDNAs encode P22 of *T. gondii*.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated DNA or RNA molecule which comprises a nucleotide sequence coding for a P22 peptide of Toxoplasma gondii, wherein said molecule comprises a nucleotide sequence selected from the group consisting of a P22 sequence:

CTTGTTTGTT GTGTTCAAGT TCGCTCTTGC
GTCCACCACC GAGACGCCAG
CGCCCATTGA GTGCACTGCC GGCGCAACGA
AGACTGTTGA TGCACCCTCC
AGTGGTTCCG TTGTCTTCCA ATGTGGGGAT
AAACTAACCA TCAGTCCCAG
TGGCGAAGGT GATGTCTTTT ATGGCAAGGA
ATGCACAGAC TCGAGGAAGT
TGACGACTGT CCTTCCAGGT GCGGTCTTGA
CAGCTAAGGT CCAGCAGCCC
GCGAAAGGTC CTGCTACCTA CACACTGTCT
TACGACGGTA CTCCCGAGAA
ACCTCAGGTT CTCTGTTACA AGTGCGTTGC
CGAAGCAGGT GCTCCCGCTG
GTCGAAATAA TGATGGTTCT AGCGCTCCGA
CGCCTAAAGA CTGCAAACTC
ATTGTTCGCG TTCCGGGTGC CGATGGCCGT
GTCACATCTG GGTTTGACCC
TGTGTCTCTC ACGGGCAAGG TTCTTGCTCC
CGGTCTCGCA GGTTTGTTGA
TCACGTTTGT G an RNA sequence having the same nucleotide sequence as said P22 sequence in which U replaces T, and a DNA and an RNA sequence complementary to said P22 sequence.

2. The molecule of claim 1, wherein said molecule is DNA.

3. The molecule of claim 1, wherein said molecule is RNA.

4. The molecule of claim 1, wherein said sequence is operatively linked to a promoter sequence.

5. The molecule of claim 4, wherein said sequence is present as part of a sequence encoding a $\beta$-galactosidase fusion product.

6. A vector comprising the molecule of claim 4.

7. A microorganism host cell transformed with the vector of claim 6.

8. The microorganism of claim 7, wherein said microorganism is an *E. coli* strain.

* * * * *